(12) United States Patent
Schmulenson et al.

(10) Patent No.: US 9,901,313 B2
(45) Date of Patent: Feb. 27, 2018

(54) SENSOR HOLDER FOR X-RAY RADIATION SENSING DEVICE

(71) Applicants: Harold K. Schmulenson, Buffalo Grove, IL (US); Thomas J. Gillen, Orland Park, IL (US)

(72) Inventors: Harold K. Schmulenson, Buffalo Grove, IL (US); Thomas J. Gillen, Orland Park, IL (US)

( * ) Notice: Subject to any disclaimer, the term of this patent is extended or adjusted under 35 U.S.C. 154(b) by 405 days.

(21) Appl. No.: 14/660,004

(22) Filed: Mar. 17, 2015

(65) Prior Publication Data

US 2015/0272524 A1 Oct. 1, 2015

Related U.S. Application Data

(60) Provisional application No. 61/970,508, filed on Mar. 26, 2014.

(51) Int. Cl.
*A61B 6/14* (2006.01)
*G03B 42/04* (2006.01)
*A61B 6/00* (2006.01)

(52) U.S. Cl.
CPC ............ *A61B 6/145* (2013.01); *A61B 6/4429* (2013.01); *G03B 42/042* (2013.01)

(58) Field of Classification Search
CPC ..... A61B 6/145; A61B 6/4429; A61B 6/4452; G03B 42/042; G03B 42/04
See application file for complete search history.

(56) References Cited

U.S. PATENT DOCUMENTS

| | | | | |
|---|---|---|---|---|
| 2,005,993 | A * | 6/1935 | Heron | G03B 42/042 378/170 |
| 2,239,569 | A * | 4/1941 | Poindexter | G03B 42/042 378/168 |
| 3,473,026 | A | 10/1969 | Updegrave | |
| D246,797 | S | 12/1977 | Jermyn | |
| 4,350,154 | A * | 9/1982 | Feldbau | A61L 9/00 128/861 |
| 4,598,416 | A * | 7/1986 | Donato | G03B 42/042 378/168 |
| 4,965,885 | A * | 10/1990 | Fuhrmann | G03B 42/042 378/168 |
| D330,254 | S | 10/1992 | Brooks | |
| 5,799,058 | A | 8/1998 | Willis et al. | |
| 6,343,875 | B1 | 2/2002 | Eppinger et al. | |
| D457,244 | S | 5/2002 | Loutis et al. | |
| D478,668 | S | 8/2003 | Epstein | |
| 6,905,244 | B2 * | 6/2005 | Kilcher | A61B 6/145 378/168 |
| D537,943 | S | 3/2007 | Schmulenson | |

(Continued)

*Primary Examiner* — Glen Kao
(74) *Attorney, Agent, or Firm* — Klintworth & Rozenblat IP LLP

(57) ABSTRACT

A sensor holder for retaining a dental radiation sensing device includes an elongated support member, at least one pair of retention guides attached to the support member, and at least one bite block attached to the support member. The retention guides are capable of holding an associated dental radiation sensing device. The bite block has a leading edge which is first inserted into a mouth of a patient and a trailing edge. The leading edge defining a recess into which structure within the mouth of the patient can seat. At least one of the retention guides may be moveable relative to the other retention guide.

16 Claims, 11 Drawing Sheets

(56) References Cited

U.S. PATENT DOCUMENTS

| | | |
|---|---|---|
| 7,226,208 B2 | 6/2007 | Schmulenson |
| 7,425,095 B2 | 9/2008 | Schmulenson et al. |
| 7,607,830 B2 | 10/2009 | Schmulenson |
| 7,607,831 B2 | 10/2009 | Schmulenson et al. |
| 7,819,579 B2 | 10/2010 | Schmulenson et al. |
| D630,328 S | 1/2011 | Fishburne, Jr. |
| 8,057,096 B2 | 11/2011 | Churchill |
| 8,142,074 B2 | 3/2012 | Schmulenson et al. |
| 8,177,428 B2 | 5/2012 | Steck et al. |
| 8,333,507 B2 | 12/2012 | Schmulenson et al. |
| 8,500,328 B2 | 8/2013 | Frampton |
| 8,602,646 B2 | 12/2013 | Frampton |
| D698,022 S | 1/2014 | Flanagan |
| D698,442 S | 1/2014 | Steward, Jr. et al. |
| 8,641,275 B2 | 2/2014 | Fenske et al. |
| 2009/0136002 A1* | 5/2009 | Schmulenson ........ G03B 42/04 378/170 |
| 2009/0245472 A1* | 10/2009 | Pichardo ................ G03B 42/04 378/168 |

* cited by examiner

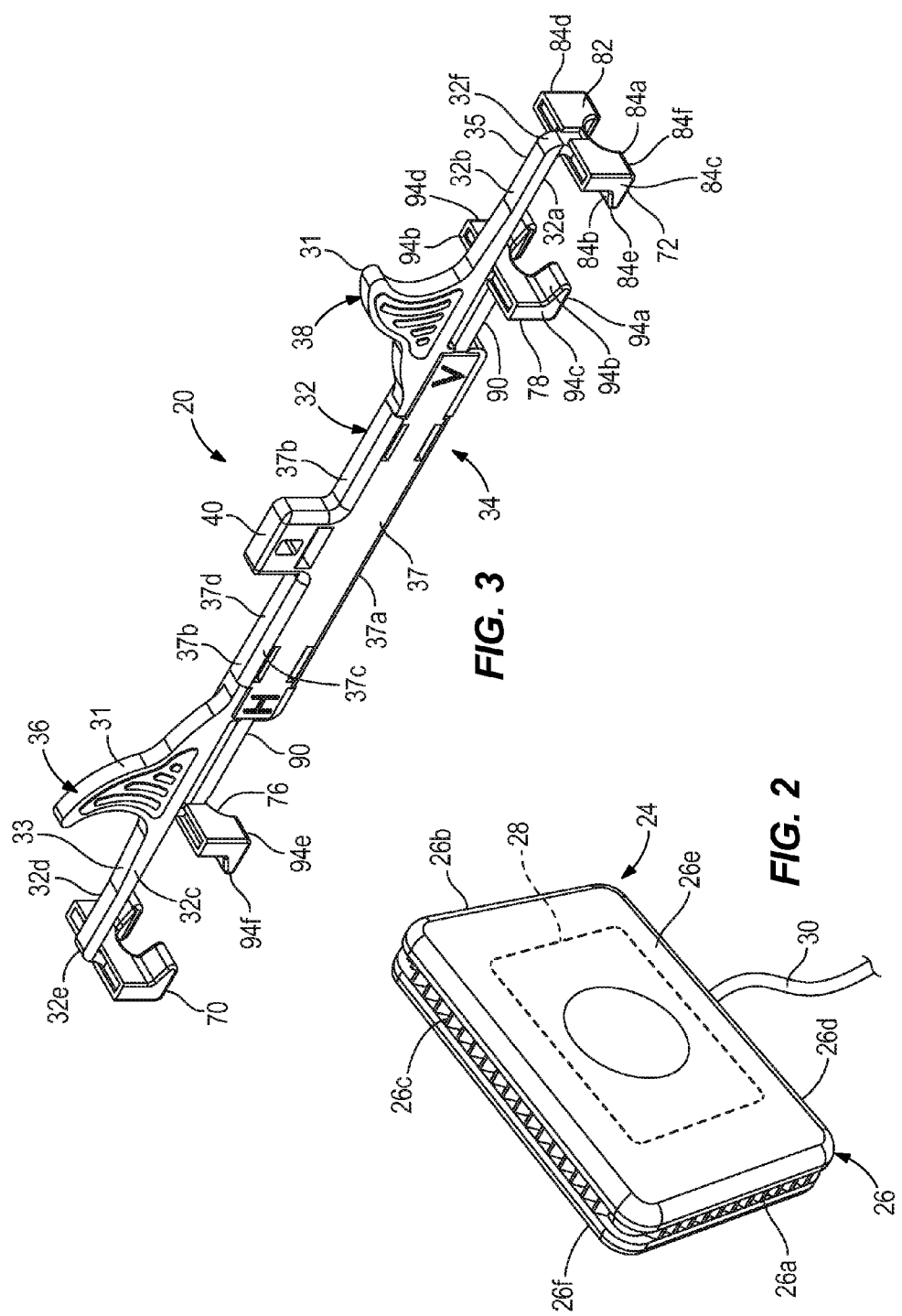

SENSOR HOLDER FOR X-RAY RADIATION SENSING DEVICE

This application claims the domestic priority of U.S. Provisional Application Ser. No. 61/970,508, filed on Mar. 26, 2014, the contents of which are incorporated herein by reference in its entirety.

FIELD OF THE DISCLOSURE

This disclosure relates generally to sensor holders, and in particular, to a sensor holder for retaining a dental radiation sensing device.

BACKGROUND

Dental radiographs are made using x-ray examination units, often including an x-ray cone or tube positioned proximate the patient and aligned to take x-rays of certain teeth. Dental x-ray sensing devices, which include including x-ray film units, digital x-ray sensors, charge coupled devices, phosphor imaging plates or the like, often have a generally flat or plate-like configuration and standardized dimensions so that the sensing device can be placed into the oral cavity.

The sensing device is placed into the patient's mouth and held in place proximate to the tooth or teeth to be examined. The x-ray's are directed through the target teeth to the sensor. It has been found that proper orientation of the sensor is required to eliminate distortions and improper focus.

To ensure proper orientation of the sensing device, sensor carriers or sensor holders with "bite blocks" have been developed. These devices often have a plate for holding the sensing device and a bite block that the patient bites down upon to position the device and the carried sensor. A bite block is shown for example, in U.S. Pat. No. 3,473,026.

Different sensing devices are often used depending upon the area of the mouth to be examined. This may include for example, endo, posterior, anterior, left, right, upper and lower bite wings, and the like. Known bite blocks and sensor holders have been individually designed and manufactured for each different type of sensing device. The dimensions of the sensing device and the sensor holder dictate the degree of secured positioning of the sensing device in the sensor holder.

A dental professional may have a large number of x-ray sensing devices with varying sizes and shapes, and hence, a similarly large number of sensor holders. The dental professional is often faced with employing a different sensing device or set of sensing devices, sensor holders and bite blocks depending upon the particular x-ray procedure being employed and the area of the mouth to be examined. At best, it is time consuming to change between sensing devices, sensor holders and bite blocks.

In order to precisely align the x-ray cone or tube with a particular x-ray sensing device held by a particular sensor holder, a rod and ring guide combination may be employed. The rod is typically attached to a particular sensor holder at one end and connected with the ring guide at the other end. The ring guide helps to aim the x-ray cone or tube at the x-ray sensing device. However, some times, in order to take x-rays of various different portions of the mouth, multiple sensor holders, bite blocks, rods and rings may need to be combined with each other to form a particular rod and ring guide combination.

SUMMARY

A sensor holder for retaining a dental radiation sensing device in accordance with some example embodiments includes an elongated support member, at least one pair of retention guides attached to the support member, and at least one bite block attached to the support member. The retention guides are capable of holding an associated dental radiation sensing device. The bite block has a leading edge which is first inserted into a mouth of a patient and a trailing edge. The leading edge defining a recess into which structure within the mouth of the patient can seat. At least one of the retention guides may be moveable relative to the other retention guide.

This Summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments

DESCRIPTION OF THE DRAWINGS

The organization and manner of the structure and operation of the disclosed embodiments, together with further objects and advantages thereof, may best be understood by reference to the following description, taken in connection with the accompanying drawings, which are not necessarily drawn to scale, wherein like reference numerals identify like elements in which:

FIG. 2 is a perspective view of a radiation sensor and/or a radiation film unit used with the sensor holder of the present disclosure;

FIG. 3 is a perspective view of the sensor holder of FIG. 1;

DETAILED DESCRIPTION

Figure 1:
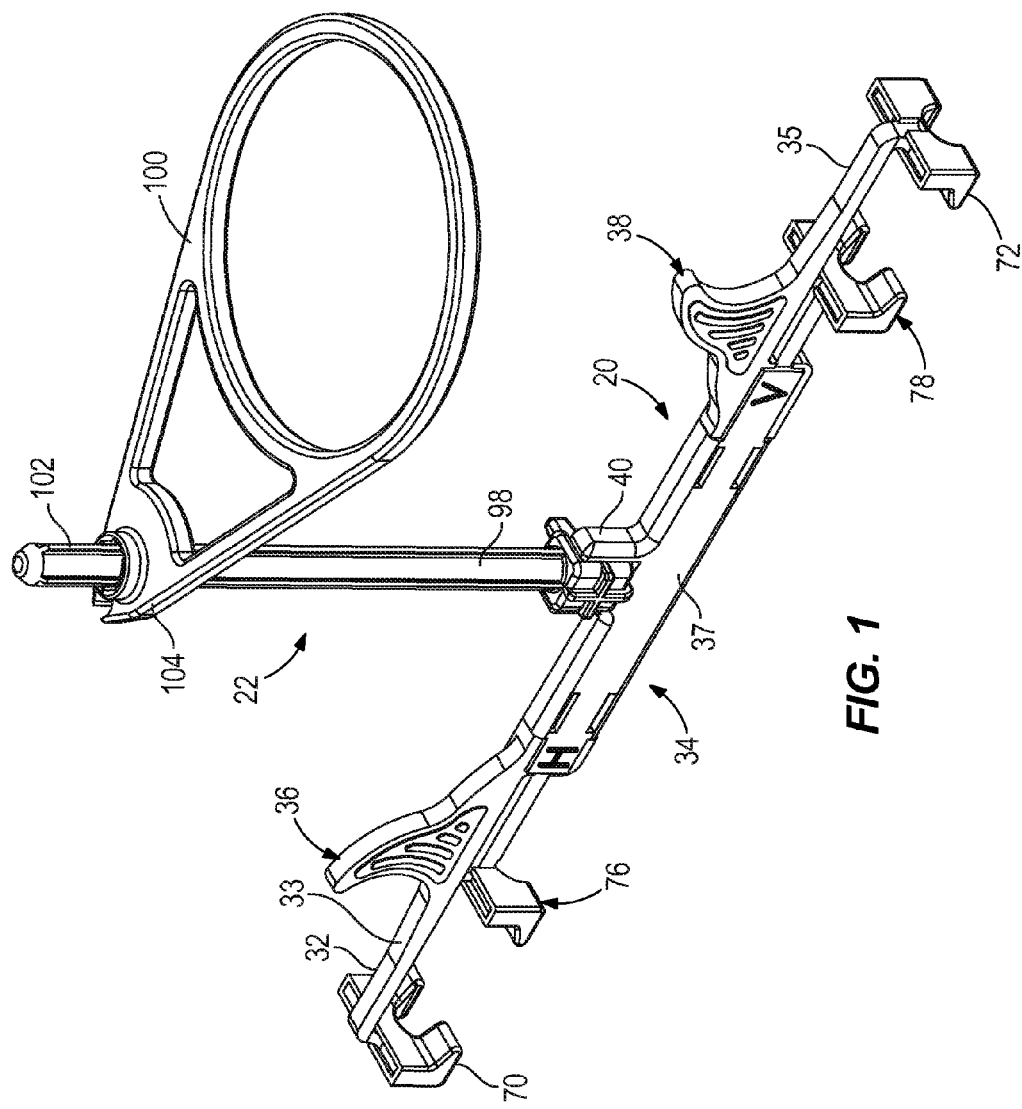
FIG. 1 is a perspective view of a sensor holder for a radiation sensor and/or a radiation film unit having a ring guide attached thereto, in accordance with a first preferred embodiment of the disclosure.
Figure 4:
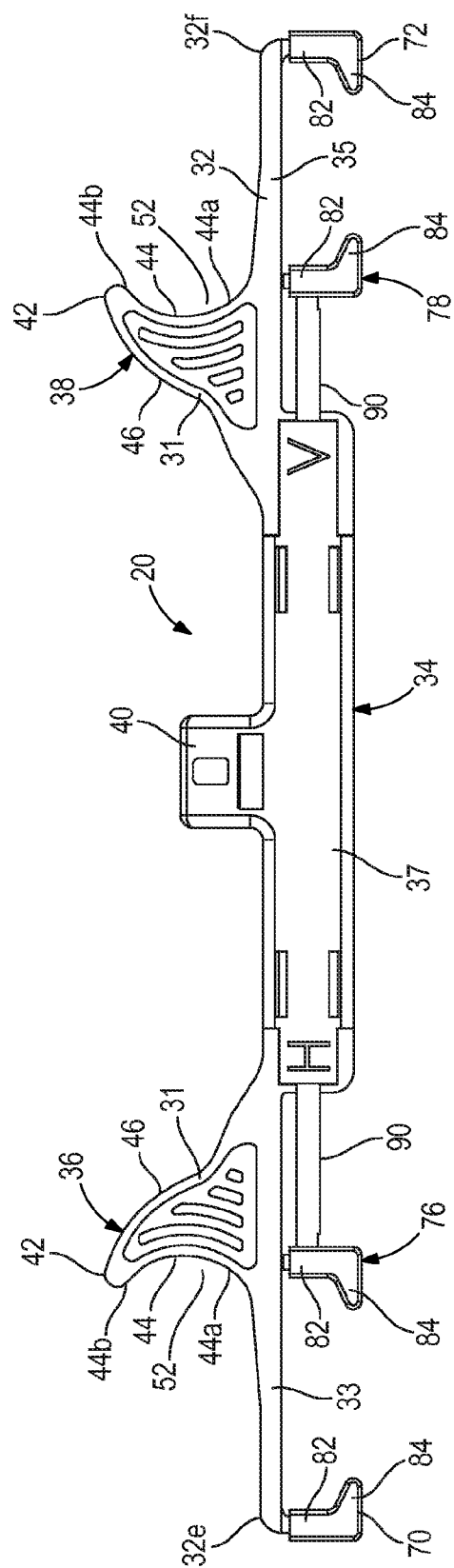
FIG. 4 is a side elevation view of the sensor holder of FIG. 1.

It should be appreciated that for simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

While the disclosure may be susceptible to embodiment in different forms, there is shown in the drawings, and herein will be described in detail, specific embodiments with the understanding that the present disclosure is to be considered an exemplification of the principles of the disclosure, and is not intended to limit the disclosure to that as illustrated and described herein. Therefore, unless otherwise noted, features disclosed herein may be combined together to form additional combinations that were not otherwise shown for purposes of brevity.

Figure 9:
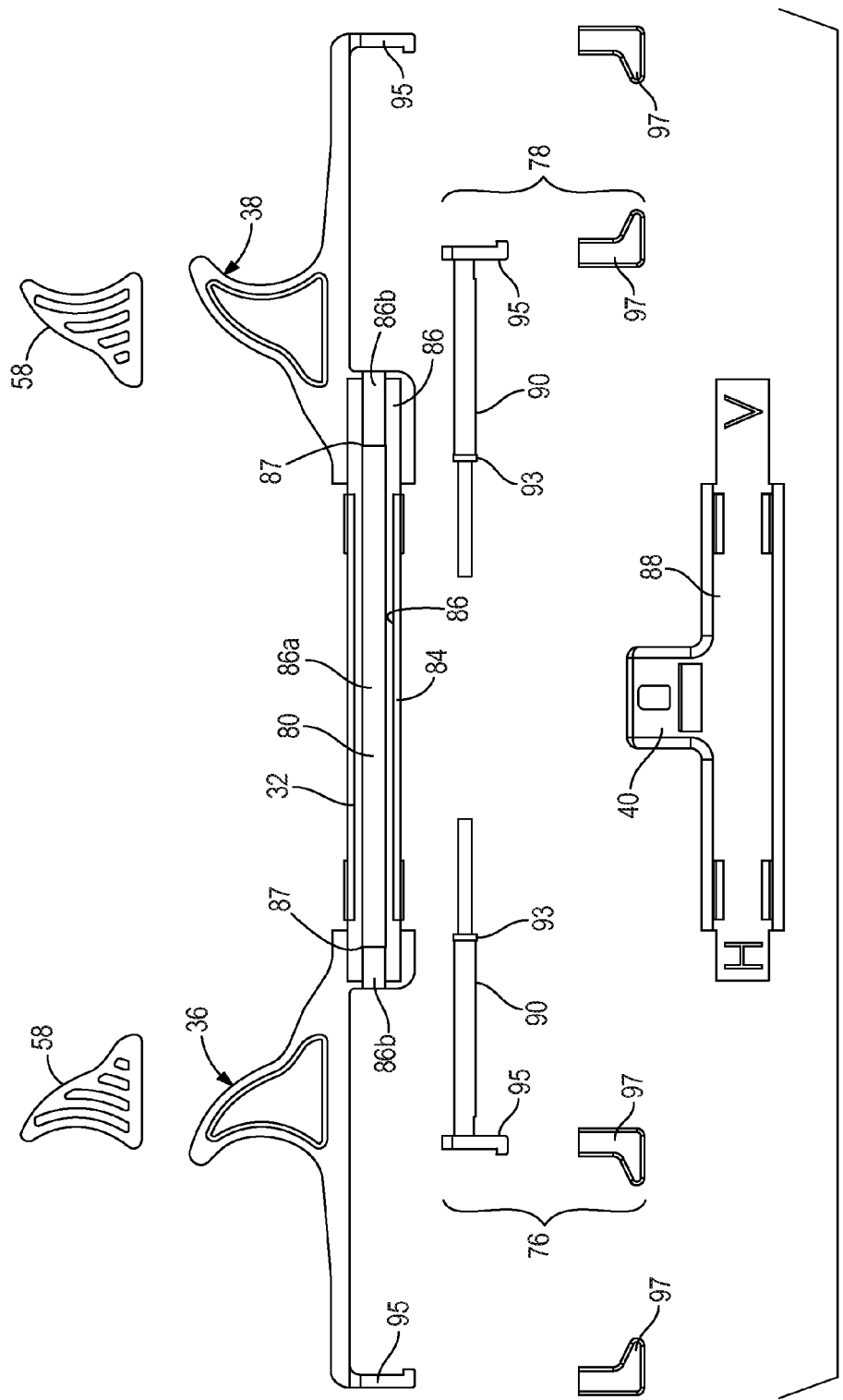
FIG. 9 is an exploded side elevation view of the sensor holder of FIG. 1.
Figure 10:
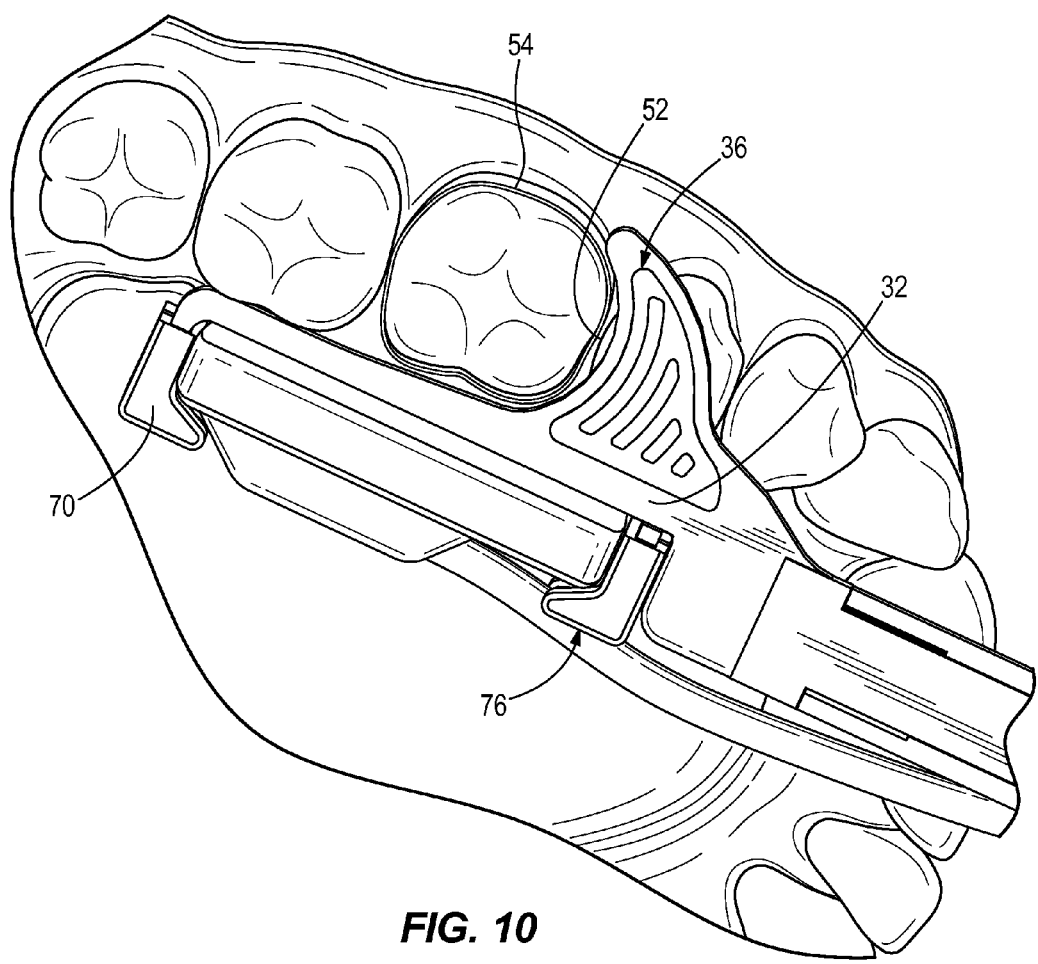
FIG. 10 is a perspective view of a sensor holder for the radiation sensor and/or a radiation film, in accordance with a second preferred embodiment of the disclosure.
Figure 11:
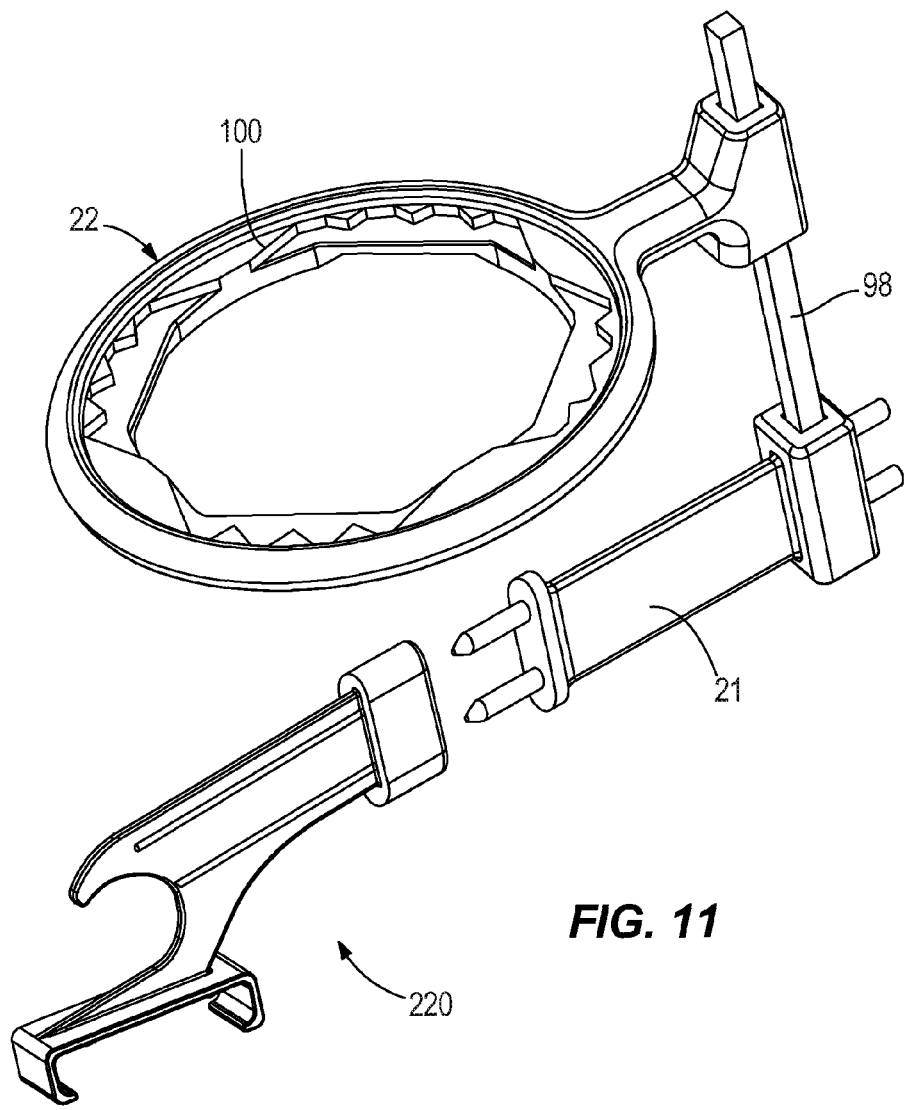
FIG. 11 is a perspective view of a sensor holder for a radiation sensor and/or a radiation film unit having a ring guide attached thereto, in accordance with a third preferred embodiment of the disclosure.
Figure 12:
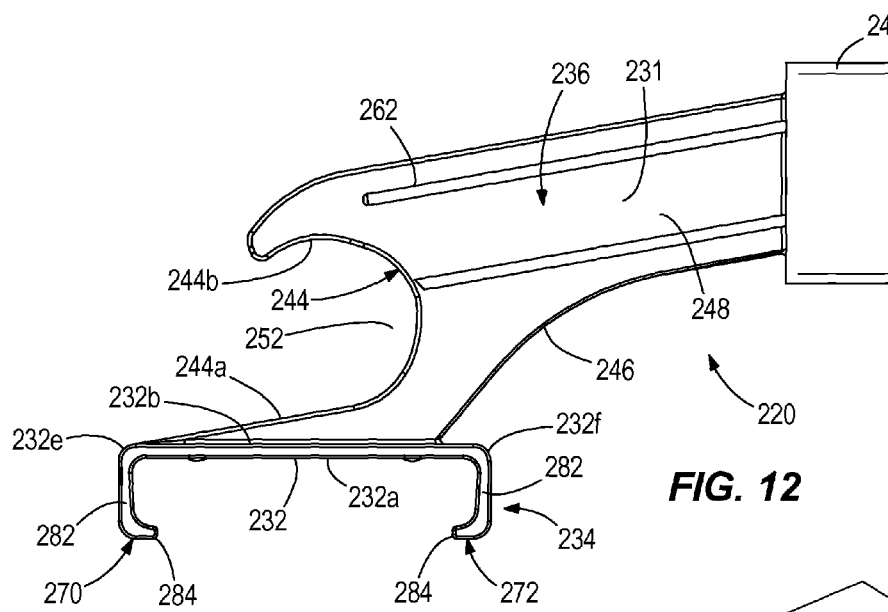
FIG. 12 is a side elevation view of the sensor holder of FIG. 11.
Figure 13:
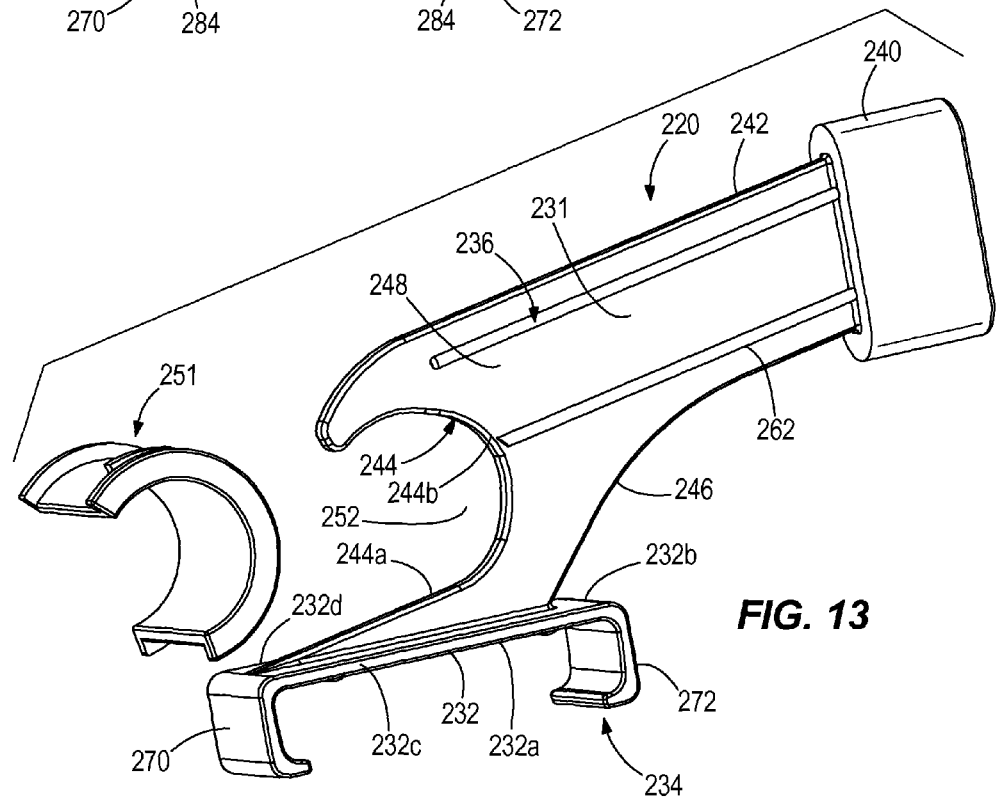
FIG. 13 is a perspective view of the sensor holder of FIG. 11, and showing a removable insert exploded therefrom.
Figure 14:
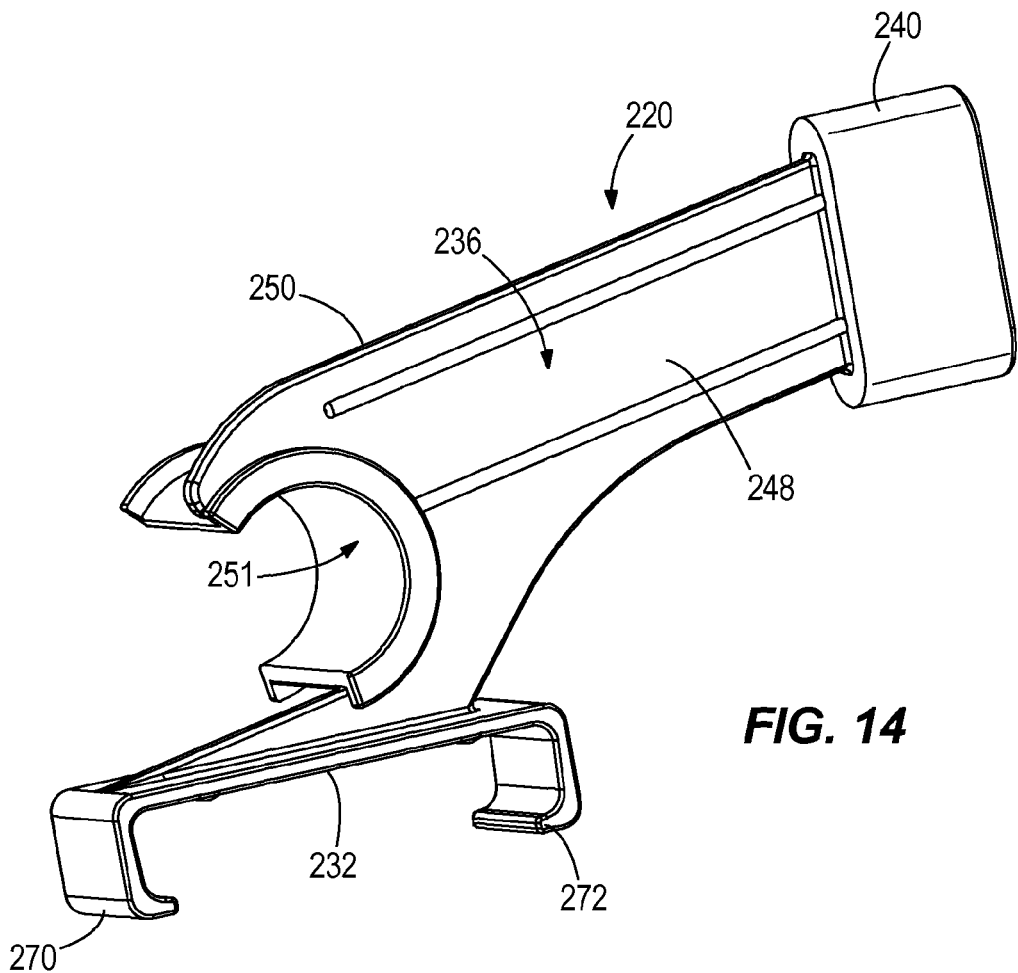
FIG. 14 is an assembled perspective view of the sensor holder and removable insert of FIG. 13.
Figure 15:
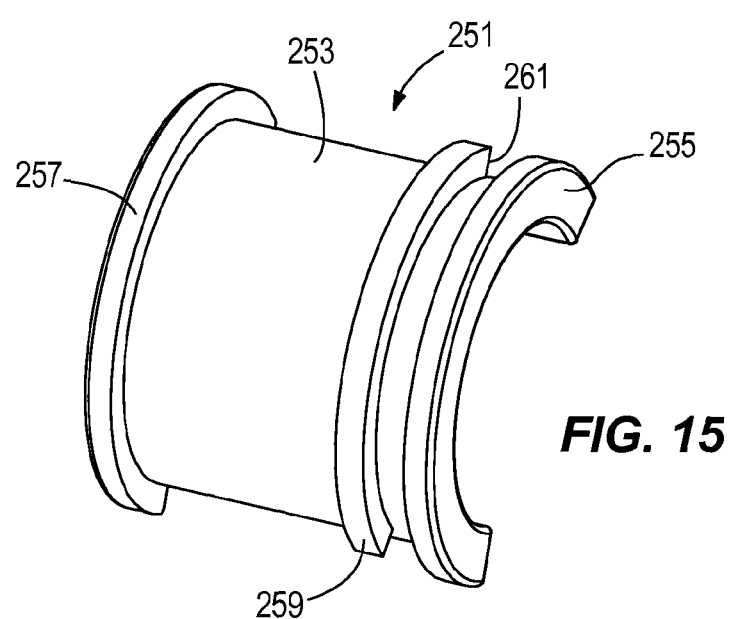
FIG. 15 is a perspective view of the removable insert of FIG. 13.

FIGS. 1 and 3-9 show a sensor holder 20 having a ring guide 22 attached thereto according to a first embodiment. FIG. 10 shows a sensor holder 20' according to a second embodiment. FIGS. 11-15 show a sensor holder 220 according to a third embodiment. Directional terms such as "upper" and "lower" and the like are used herein for ease in description of the sensor holder 20, 20', 220, but do not denote a require orientation of the sensor holder 20, 20', 220 during use. The sensor holder 20, 20', 220 is used to hold a radiation sensing device 24 for taking x-rays of a patient's mouth during a medical procedure, such as during a dental, endodontic or orthodontic procedure.

The radiation sensing device 24 is any device which can be used to sense radiation, such as gamma wave radiation, light wave radiation and, preferably, x-ray radiation. The radiation sensing device 24 preferably includes a housing 26 which surrounds either a radiation film unit or a radiation sensor unit 28. The radiation film unit uses film to detect radiation, such as x-ray radiation. The radiation sensor unit uses a digital sensor or a charge coupled device to detect radiation such as x-rays, a phosphor imaging plate or the like. Radiation sensor unit may include a wire 30 which is used to provide power and/or transfer signals between the digital radiation sensor and a control unit, not shown. Preferably, radiation sensing device 24 is a dental x-ray sensing device which is sized for use in the mouth of a patient in order to take x-ray scans of a patient's teeth. Radiation sensing devices 24 can vary in width, height and thickness. Preferably the width of the radiation sensing device 24 is between 3 and 8 centimeters. Also preferably the height of the radiation sensing device 24 is between 1 and 4 centimeters and the thickness is preferably between 0.1 and 20 millimeters, and more preferably, between 1 to 10 millimeters.

As shown, the housing 26 is rectangular having opposite side edges 26a, 26b, an upper edge 26c, a bottom edge 26c, a front face 26d and a rear face 26e. The housing 26 may take other shapes, such as round or square. Preferably, the housing 26 completely envelopes the radiation film unit or the radiation sensor unit 28, however, the housing 26 may have a window, or a plurality of windows exposing a portion of the radiation film unit or the radiation sensor unit 28. Preferably, the housing 26 is manufactured using an injection molded process in order to reduce costs, however, the housing 26 can be manufactured in one of many ways. For example, housing 26 may be machined, thermoformed, and hand-made. Preferably, in order to reduce costs and maintain rigidity, housing 26 is a one-piece unit which is integrally formed, or a two-piece unit which is snap-fit together. However, housing 26 may comprise multiple parts which are then assembled and fitted together. Preferably, housing 26 is constructed from a rigid yet somewhat flexible material through which radiation can pass, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The housing 26 may be colored any one of various different colors depending on the size and type of sensors used. For example, the housing 26 may be colored white for a size two x-ray film unit or colored green for a size zero x-ray film unit.

The sensor holder 20, 20', 220 is designed to hold and retain the radiation sensing device 24 in a multitude of positions. Preferably, the sensor holder 20, 20', 220 is manufactured using an injection molded process in order to reduce costs, however, the sensor holder 20, 20', 220 can be manufactured in one of many ways. For example, the sensor holder 20, 20', 220 may be machined, thermoformed, and hand-made. Preferably, sensor holder 20, 20', 220 is constructed from a rigid yet somewhat flexible material, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The sensor holder 20, 20', 220 may be colored any one of various different colors depending on the size and type of sensors used. For example, the sensor holder may be colored white for a size two x-ray film unit or colored green for a size zero x-ray film unit.

Attention is invited to the first embodiment of the sensor holder 20 shown in FIGS. 1 and 3-9. The sensor holder 20 includes an elongated support member 32, a retention assembly 34 attached to the support member 32, first and second bite blocks 36, 38 attached to the support member 32, and a mount 40 extending from the support member 32 for mounting the ring guide 22. The mount 40 is preferably positioned at the midpoint of the support member 32. The retention assembly 34 is used to hold the radiation sensing device 24 as described herein. A patient bites onto one of the bite blocks 36, 38 to hold the sensor holder 20 in the mouth of the patient.

The support member 32 has end portions 33, 35 with a central portion 37 therebetween.

Each end portion 33, 35 has front and back surfaces 32a, 32b which defines a width of the end portions 33, 35, an upper surface 32c extending between the front and back surfaces 32a, 32b, a lower surface 32d extending between the front and back surfaces 32a, 32b. The support member 32 has first and second opposite ends 32e, 32f. The distance between the upper surface 32c and the lower surface 32d defines a height $H_1$ of the support member 32, see FIG. 7.

The central portion 37 has front and back surfaces 37a, 37b which defines a width, an upper surface 37c extending between the front and back surfaces 37a, 37b, a lower surface 37d extending between the front and back surfaces 37a, 37b. The central portion 37 is wider than end portions 33, 35. An open-ended central passageway 86 extends through the central portion 37. The passageway 86 has a central portion 86a which has a larger diameter than end portions 86b extending from the central portion 86a to the open ends of the passageway 86. As such, a pair of shoulders 87 are provided in the passageway 86. Preferably, central portion 37 may be formed of two parts, a wall 83 and a removable cover 88 attached thereto as is shown in FIG. 9.

The cover 88 can be attached to the wall 83 by a snap fit, glue, sonic welding or mechanically fastened together, for example. If provided as two parts, the mount 40 may be provided on the cover 88 as shown, or on the support member 32.

The bite block 36 is positioned between the mount 40 and the first end 32*e* of the support member 32. The bite block 38 is positioned between the mount 40 and the second end 32*f* of the support member 32. Each bite block 36, 38 is formed of a body 31 having a front surface which is integrally formed with the back surface 32*b* of the support member 32, an opposite back surface 42, a leading end surface 44 extending between the front and back surfaces, a trailing end surface 46 extending between the front and back surfaces, an upper surface 48 and a lower surface 50. The distance between the upper surface 48 and the lower surface 50 defines a height $H_2$, see FIG. 7, of each bite block 36, 38. Each bite block 36, 38 preferably has approximately the same height $H_1$ as the support member 32. The bite blocks 36, 38 are identically formed, except that the bite block 36 is the mirror image of the bite block 38. As such, the trailing end surfaces 46 of the bite blocks 36, 38 face each other.

Each body 31 is shaped such that the leading end surface 44 provides a recess 52 which accommodates any structure 54 mounted on a patient's tooth, such as a clamp for a dental dam, therein as shown in FIG. 10. The shape of the body 31 is not critical, other than the leading end surface 44 provides the recess 52. That is, the leading end surface 44 has a first section 44*a* which is shaped to abut against a side of the structure 54 and has a second section 44*b* which extends around and overlaps an outer side of the structure 54. The rear surface 32*b* of the support member 32 is proximate to the inner side of the structure 54. As shown in a preferred embodiment, the bite blocks 36, 38 generally look like a "shark fin", with first and second sections 44*a*, 44*b* that extend along the same curve, and a trailing end surface 46 which curves outwardly and toward the end 32*e*, 32*f* of the support member 32. As such, the shape of each bite block 36, 38 generally mimics the dental arch of the patient. Other shapes are possible, such as that shown in FIG. 6, where the first section 44*a* is perpendicular or angled relative to the support member 32 and the second section 44*b* is perpendicular or angled relative to the first section 44. Either section 44*a*, 44*b* may have a curved surface.

When the sensor holder 20 is inserted into a patient's mouth, the patient is able to bite down with the patient's teeth on the surfaces 48, 50 of the bite block 36, 38. The bite block 36, 38 allows for more accurate positioning of the sensor holder 20, and more specifically the sensor 28, within a patient's mouth. Preferably, the bite block 36, 38 includes a series of serrations 62 in order to provide additional grip and less movement for the sensor holder 20 within the patient's mouth. Preferably, the serrations 62 are curved slots and are indented into the bite block 36, 38. The serrations 62 may take a variety of other forms, such as diamond-shaped, cubes, straight lines etc. As shown, the trailing end surface 46 curves outwardly and toward the end 32*e*, 32*f* of the support member 32. Curving this trailing end surface 46 may increase patient comfort as the patient's tongue may brush against this curved surface.

Figure 5:
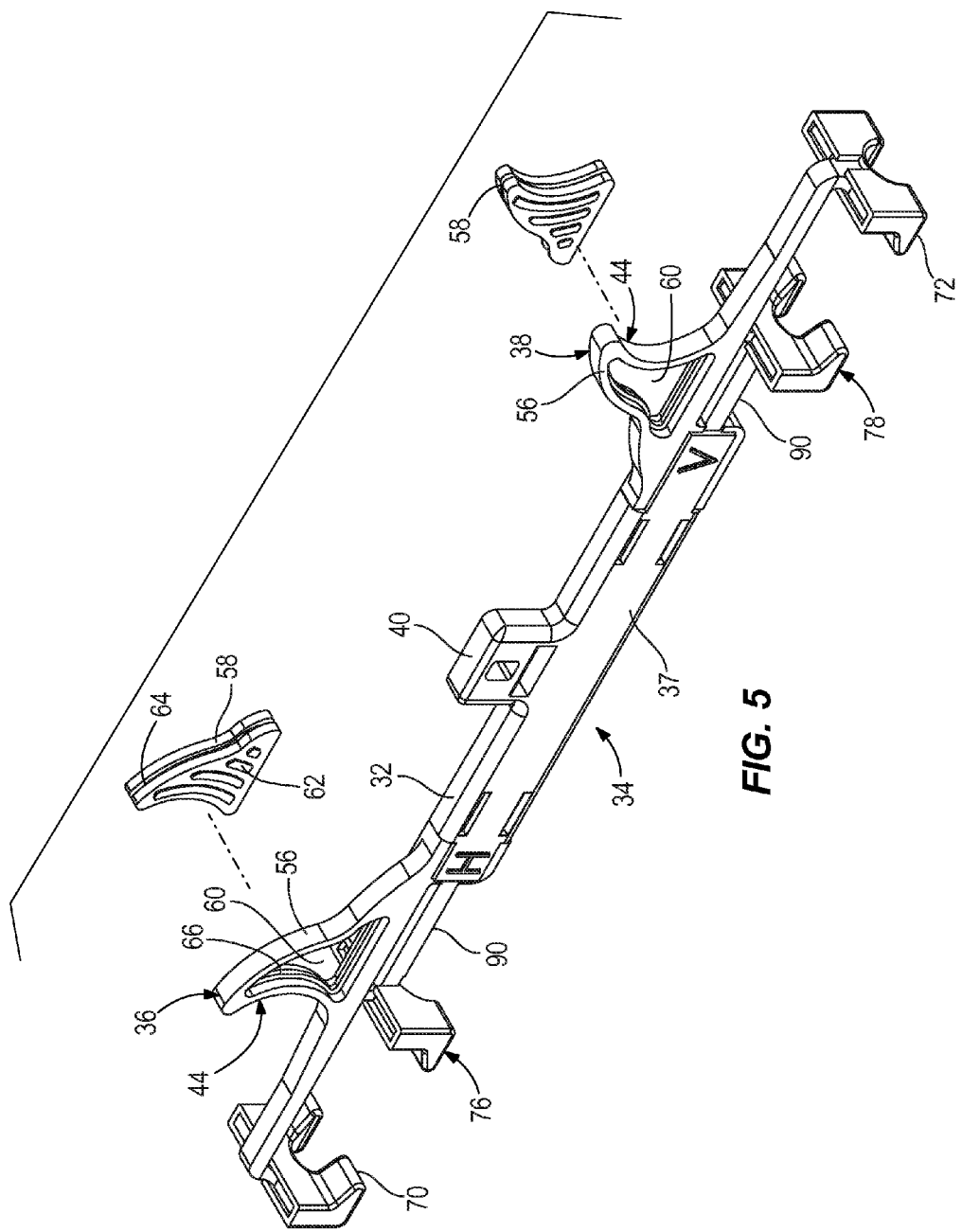
FIG. 5 is an exploded perspective view of the sensor holder of FIG. 1.
Figure 6:
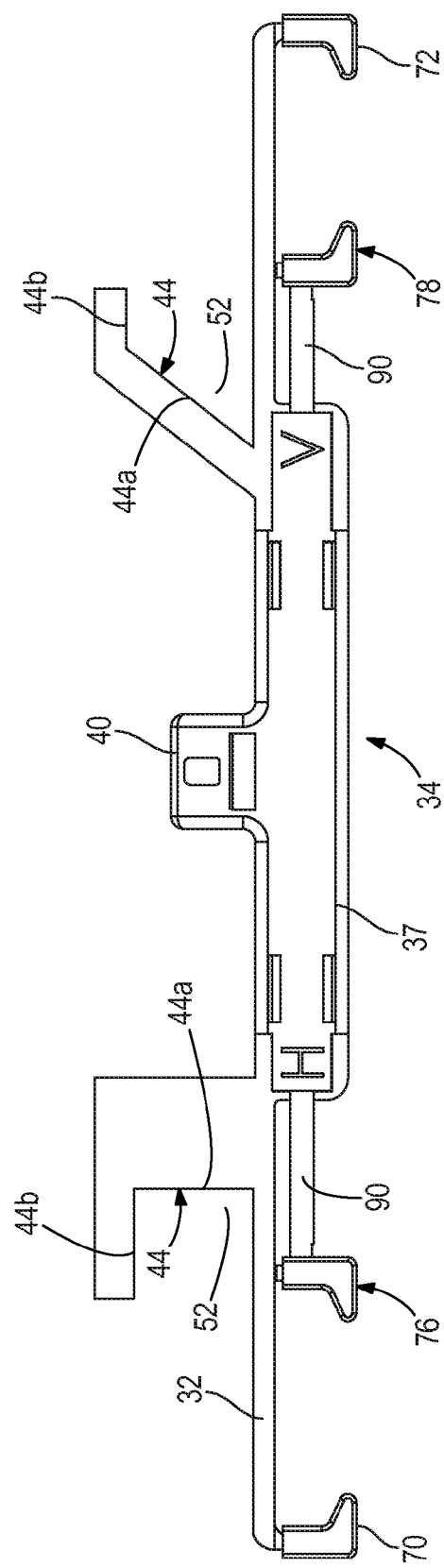
FIG. 6 is a side elevation view of an alternate sensor holder to that shown in FIG. 1.

The bite block 36, 38 may be formed in two parts, or may be integrally formed as a single piece. One example of when the bite block 36, 38 is formed of two parts is that the bite block 36, 38 has a frame 56 which is attached to the support member 32, and an insert 58 which mounts in the frame 56. The frame 56 defines an outer shape which is the same as shown in FIGS. 5 and 9, but includes a central aperture 60 into which the insert 58 is mounted. The insert 58 may be formed of a soft material, such as an elastomeric material, for example, rubber or silicone. The insert 58 mirrors the shape of the central aperture 60 and when inserted, the insert 58 fills the central aperture 60. The insert 58 can be held in the central aperture 60 by a variety of means, such as friction fit, by medical grade adhesive. As shown, the insert 58 has a groove 64 into which seats within a protruding bead 66 in the wall forming the central aperture 60 to further a friction fit between the insert 58 and the frame 56. The soft material of which the insert 58 is made provides a cushioning feel to the patient when the patient bites onto the bite block 36, 38. The insert 58 may have the serrations 62 thereon. While the groove 64 is shown on the insert 58 and the bead 66 on the frame 56, it is to be understood that the bead 66 can be provided on the insert 58 and the groove 64 on the frame 56. The bite block 36, 38 may be integrally formed and have a soft material attached to the upper and/or lower surfaces 48, 50 thereof.

The retention assembly 34 includes first and second retention guides 70, 72 extending from the front side 32*a* of the support member 32, plungers 90 which are mounted in the passageway 86 of the central portion 37 of the support member 32 and which extend therefrom, the third and fourth retention guides 76, 78 attached to the plungers 90, and a biasing member 80 mounted within the central portion 37.

The first retention guide 70 extends from the front side 32*a* of the support member 32 proximate to the first end 32*e* of the support member 32. The second retention guide 72 extends from the front side 32*a* of the support member 32 at the second end 32*f* of the support member 32.

Each plunger 90 is an elongated member having a first free end and a second end on which the respective retention guide 76, 78 is mounted. Each plunger 90 has an enlarged shoulder 93 provided along its length. Each plunger 90 seats within the passageway 86 and the respective retention guide 76, 78 seats outside of the passageway 86. Each plunger 90 is slideable relative to the central portion 37 to move the respective retention guide 76, 78 toward and away from the respective first and second retention guides 70, 72. The shoulders 93 of the plungers 90 are capable of engaging with the shoulder 87 in the passageway 86 when the respective retention guide 76, 78 is moved toward the shoulder 87. This prevents the plungers 90 from falling out of the central portion 37.

The biasing member 80 may take a variety of forms, such as a spring or an elastomeric member. The biasing member 80 is housed within the central portion 86*a* of the passageway 86 such that the biasing member 80 is positioned between the ends of the plungers 90. If the biasing member 80 is formed as a spring, the biasing member 80 can encircle the ends of the plungers 90 and abut against the shoulders 93 of the plungers 90. This will aid in preventing the spring from buckling within the central portion 37. The biasing member 80 controls the amount of linear movement of third and fourth retention guides 76, 78.

Figure 7:
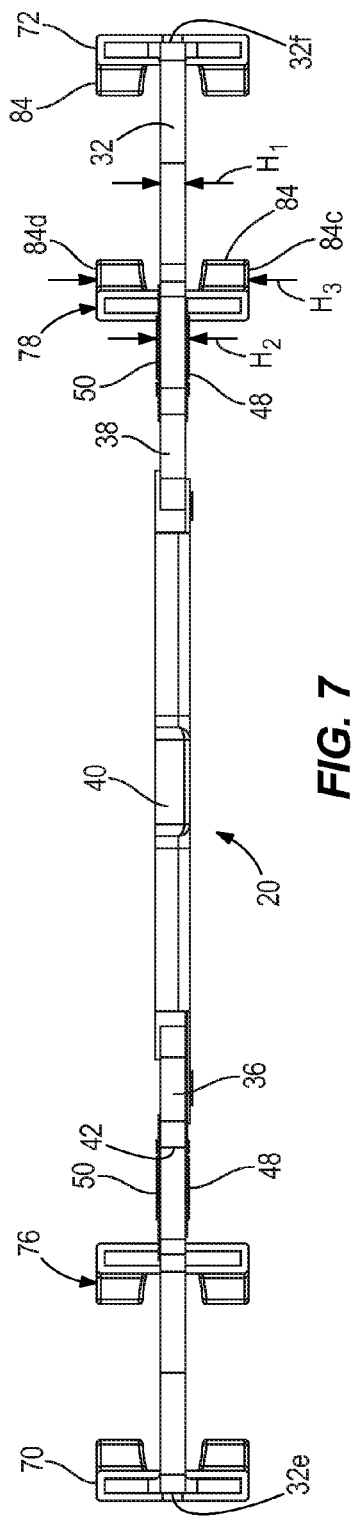
FIG. 7 is a top plan view of the sensor holder of FIG. 1.
Figure 8:
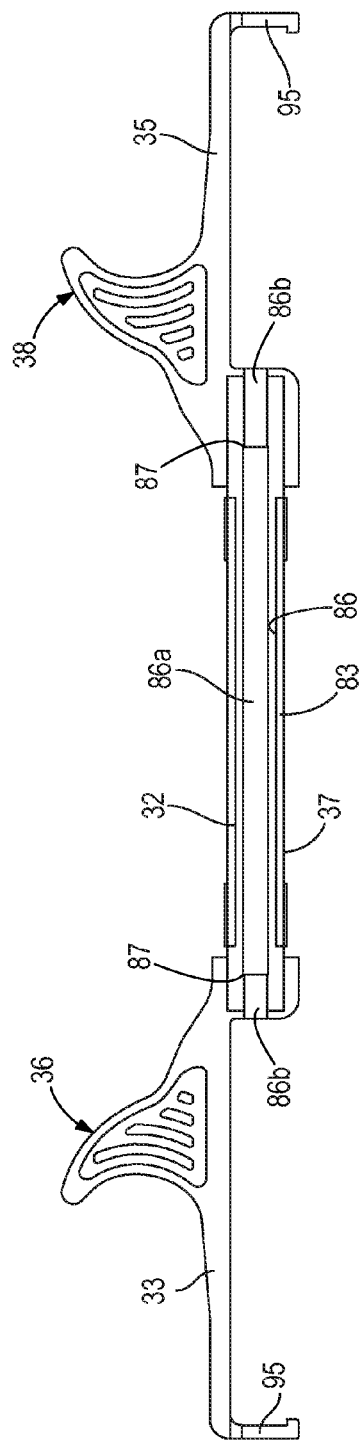
FIG. 8 is a side elevation view of a portion of the sensor holder of FIG. 1.

Preferably, each retention guide 70, 72, 76, 78 is formed from a generally L-shaped cross-section having an extending portion 82 which extends perpendicularly relative to the support member 32 and a gripping portion 84 which extends perpendicularly from the extending portion 82 and is parallel to or curves inwardly toward the support member 32. The support member 32 is preferably positioned at the midpoint of the retention guide 70, 72, 76, 78 as best shown in FIG. 7. Each gripping portion 84 has front and back surfaces 84*a*, 84*b*, an upper surface 84*c* extending between the front and back surfaces 84*a*, 84*b*, a lower surface 84*d* extending between the front and back surfaces 84a, 84b, and first and second opposite ends 84e, 84f. The distance between the upper surface 84c and the lower surface 84d defines a height $H_3$, see FIG. 7, of each gripping portion 84. The gripping portions 84 may curve inwards towards the support member 32 as is known in the art. The height $H_1$ of the support member 32 is significantly smaller than the height $H_3$ of the gripping portions 84.

Each retention guide 70, 72, 76, 78 may be formed as a single piece, or may be formed as two pieces. When formed as two pieces, each retention guide 70, 72, 76, 78 has a base member 95 with an overlay 97 mounted thereon. The base member 95 on retention guides 70, 72 is integrally formed with the support member 32. The base member 95 on retention guides 76, 78 is integrally formed with the plunger 90. The overlay 97 provides the extending portion 82 and the gripping portion 84. The overlay 97 is preferably formed of an elastomeric material, for example, rubber or silicone.

The first retention guide 70 is proximate to, but spaced from the third retention guide 76 and thus form a first set of retention guides; the second retention guide 72 is proximate to, but spaced from, the fourth retention guide 78 and thus form a second set of retention guides. The ends 84e face each other in each set of retention guides. When the biasing member 80 is uncompressed, the bite blocks 36, 38 are generally aligned with the portion of the plungers 90 which are not in the central portion 37 and are further aligned with the third and fourth retention guides 76, 78. The third and fourth retention guides 76, 78 can be moved toward each other to the extent that the biasing member 80 allows such movement. The radiation sensing device 24 may be mounted between the first and third retention guides 70, 76 or may be mounted between the second and fourth retention guides 72, 78. Preferably, the gripping portions 84 apply enough pressure on the radiation sensing device 24 to hold the radiation sensing device 24 in place without damaging the radiation sensing device 24. With this configuration, the sensor holder 20 can receive the radiation sensing device 24, by sliding the radiation sensing device 24 in between the first and third retention guides 70, 76 and against the support member 32. Alternatively, the sensor holder 20 can receive the radiation sensing device 24, by sliding the radiation sensing device 24 in between the second and fourth retention guides 72, 78 and against the support member 32. As shown in the drawings, the space between the first and third retention guides 70, 76 is greater than the space between the second and fourth retention guides 72, 78 when the biasing member 80 is uncompressed. In general, the user would place a horizontally-arranged radiation sensing device 24 between the first and third retention guides 70, 76, and the user would place a vertically-arranged radiation sensing device 24 between the second and fourth retention guides 72, 78.

When the radiation sensing device 24 is mounted in between the first and third retention guides 70, 76, the third retention guide 76 may move toward the central portion 37 by biasing the biasing member 80 to accommodate the size of the radiation sensing device 24 if the radiation sensing device 24 is larger than the distance between the first and third retention guides 70, 76 when the biasing member 80 is uncompressed. This accommodates a large number of sizes of radiation sensing guides 24 between the first and third retention guides 70, 76. When the radiation sensing guide 24 is mounted between the first and third retention guides 70, 76, the sensor 28 preferably is positioned above or below the support member 32 so that the support member 32 does not impede the image taken by the radiation sensing guide 24. If the sensor 28 does overlap the support member 32, because the height of the support member 32 is significantly smaller than the height of the gripping portions 84, a large amount of material is not present behind the sensor 28, thereby lessening the impact of the material of the support member 32 on the image taken. The height of the bite block 36 is also significantly smaller than the height of the gripping portions 84 so that a large amount of material of the bite block 36 is not present behind the sensor 28, thereby lessening the impact of the material of the bite block 36 on the image taken.

Likewise, when the radiation sensing device 24 is mounted in between the second and fourth retention guides 72, 78, the fourth retention guide 78 may move toward the central portion 37 by biasing the biasing member 80 to accommodate the size of the radiation sensing device 24 if the radiation sensing device 24 is larger than the distance between the second and fourth retention guides 72, 78 when the biasing member 80 is uncompressed. This accommodates a large number of sizes of radiation sensing guides 24 between the second and fourth retention guides 72, 78. When the radiation sensing guide 24 is mounted between the second and fourth retention guides 72, 78, the sensor 28 preferably is positioned above or below the support member 32 so that the support member 32 does not impede the image taken by the radiation sensing guide 24. If the sensor 28 does overlap the support member 32, because the height of the support member 32 is significantly smaller than the height of the gripping portions 84, a large amount of material is not present behind the sensor 28, thereby lessening the impact of the material of the support member 32 on the image taken. The height of the bite block 38 is also significantly smaller than the height of the gripping portions 84 so that a large amount of material of the bite block 38 is not present behind the sensor 28, thereby lessening the impact of the material of the bite block 38 on the image taken.

In one embodiment, the length from one end 32e of the sensor holder 20 to the opposite end 32f of the sensor holder 20 is approximately between 5 and 50 centimeters and more preferably between 10 and 30 centimeters and most preferably between 15 and 25 centimeters. Additionally, a distance between the first retention guide 70 and the third retention guide 76 is preferably between 3 and 8 centimeters, and a distance between the second retention guide 72 and the fourth retention guide 78 is preferably between 3 and 8 centimeters. A distance between the support member 32 and a far end of the retention guide 70, 72, 76, 78 is preferably between 1 and 20 millimeters, and more preferably, between 2 to 10 millimeters. A distance from the back surface 32b of the support member 32 to the back surface 42 of the bite block 36, 38 is preferably between 1 and 3 centimeters.

In one embodiment, a system for holding and aligning the radiation sensing device 24 is provided. The system includes the sensor holder 20, the mount 40, and the ring guide 22. The ring guide 22 includes a rod 98 removably connected with the mount 40, and a ring 100 which is slidably connected with the rod 98. Rod 98 connects the ring 100 with the support member 32 through the use of the mount 40. Preferably, the rod 98 is composed of a rigid material such as a plastic, or a metal, for example aluminum, steel, or nickel. The rod 98 allows the ring 100 to be positioned a distance away from the support member 32. Preferably, the rod 98 is slidably connected with the ring 100 through a channel 102 which is formed through a connecting portion 104 of the ring 100. This allows the distance between the ring 100 and either the sets of the retention guides 70/76 and 72/78 to be varied. Other mounts for attaching the rod 98 and ring 100 are within the scope of the present disclosure.

The rod 98 preferably has a multi-sided cross section, such as a square cross-section, to prevent the ring 100 from rotating on the rod 98 and to provide precise alignment between the support member 32 and the ring 100. The rod 98 and the ring 100 can be any standard or known arrangement of rods and ring guides and includes such devices as those shown in U.S. Pat. No. 3,473,026; the XCP Film Holding System manufactured by Dentsply Rinn™ of Elgin, Ill.; and the RAPD Positioning System™ manufactured by Flow X-Ray Corporation of Deer Park, N.Y.

The ring 100 is used to precisely aim a radiation generating machine, such as an x-ray machine, at and direct radiation from the radiation generating machine to either set of retention guides. The ring 100 is a generally circular member which is used to aim and align a cone of a radiation generating machine with either set of retention guides 70/76 and 72/78, so that radiation emitted from the machine is precisely directed towards the radiation sensing device 24 situated in either set of retention guides 70/76 and 72/78.

There are three basic positions to place the ring 100 in with respect to either set of retention guides 70/76 and 72/78 for taking three basic types of radiographs: 1) a central position in which the ring 100 is aimed at the center of either set of retention guides 70/76 and 72/78 for taking bite wing or anterior type radiographs, a lower position in which the ring 100 is aimed at the a lower portion of either set of retention guides 70/76 and 72/78 for taking lower posterior type radiographs; and an upper position, which is opposite the lower position, in which the ring 100 is aimed at an upper portion of either set of retention guides 70/76 and 72/78 for taking upper posterior type radiographs.

It is to be understood that while two sets of retention guides 70/76 and 72/78 are provided on the sensor holder, only a single set of retention guides, for example set 70/76, could be provided.

In operation, the radiation sensing device 24 is inserted into one set of retention guides 70/76 and 72/78 of the sensor holder 20. As first described, the radiation sensing device 24 is inserted into between retention guides 70/76. During insertion of the radiation sensing device 24 into the sensor holder 20, third retention guide 76 can move to accommodate the size of the radiation sensing device 24. The sensor holder 20 and the attached radiation sensing device 24 are then inserted into the mouth of the patient. During insertion of the sensor holder 20 into the patient's mouth, the sensor holder 20 is inserted with the leading end surface 44 of the bite block 36 first going into the mouth, with the trailing end surface 46 following. The bite block 36 passes over the teeth of the patient and the support member 32, the retention guides 70, 76 and the radiation sensing device 24 are in the interior of the mouth. As can be seen in the drawings, there is nothing aligned with the bite block 36 along the length of the sensor holder 20 between the end 32e of the sensor holder 20 and the bite block 36. Therefore, the sensor holder 20 can be easily inserted into the mouth of the patient merely by sliding the sensor holder 20 into the mouth until bite block 36 is properly positioned or the bite block 36 encounters an obstacle, such as structure 54, in the mouth. When the bite block 36 is correctly positioned, the patient bites down onto the bite block 36 to securely hold the sensor holder 20 in place. Alternatively, the radiation sensing device 24 is inserted into between retention guides 72/78. During insertion of the radiation sensing device 24 into the sensor holder 20, fourth retention guide 78 can move to accommodate the size of the radiation sensing device 24. The sensor holder 20 and the attached radiation sensing device 24 are then inserted into the mouth of the patient. During insertion of the sensor holder 20 into the patient's mouth, the sensor holder 20 is inserted with the leading end surface 44 of the bite block 38 first going into the mouth, with the trailing end surface 46 following. The bite block 38 passes over the teeth of the patient and the support member 32, the retention guides 70, 76 and the radiation sensing device 24 are in the interior of the mouth. As can be seen in the drawings, there is nothing aligned with the bite block 38 along the length of the sensor holder 20 between the end 32f of the sensor holder 20 and the bite block 38. Therefore, the sensor holder 20 can be easily inserted into the mouth of the patient merely by sliding the sensor holder 20 into the mouth until bite block 38 is properly positioned or the bite block 38 encounters an obstacle, such as structure 54, in the mouth. When the bite block 38 is correctly positioned, the patient bites down onto the bite block 38 to securely hold the sensor holder 20 in place.

If the patient has structure 54, such as a clamp, on a tooth to be x-rayed, when the bite block 36 or 38 encounters the structure 54, the structure 54 seats within the recess 52. The bite block 36 or 38 partially surrounds and engages the structure 54 ensuring a proper fit.

Attention is now invited to the second embodiment of the sensor holder 20' shown in FIG. 10. In this embodiment, the retention guides 70, 76 are both integrally formed with the support member 32 such that both retention guides 70, 76 extend from the support member 32 like that of retention guide 70 in the first embodiment. A like set of retention guides can be formed on the opposite end of the sensor holder 20'.

Attention is now invited to the third embodiment of the sensor holder 220 shown in FIGS. 11-15. The sensor holder 220 is adapted for use with a ring guide adapter 21 and its associated ring guide 22 such as that shown in U.S. Pat. No. 8,333,507, which disclosure is incorporated by reference herein in its entirety. The sensor holder 220 holds the radiation sensing device 24.

The sensor holder 220 includes an elongated support member 232, a retention assembly 234 attached to a front side 232a of the support member 232, a bite block 236 attached to a back surface 232b of the support member 232 and to a mount 240 for mounting the ring guide 22. The retention assembly 234 is used to hold the radiation sensing device 24 as described herein. A patient bites onto the bite block 236 to hold the sensor holder 220 in the mouth of the patient.

The support member 232 has front and back surfaces 232a, 232b, an upper surface 232c extending between the front and back surfaces 232a, 232b, a lower surface 232d extending between the front and back surfaces 232a, 232b, and first and second opposite ends 232e, 232f. The distance between the upper surface 232c and the lower surface 232d defines a height of the support member 232.

The bite block 236 is positioned between the mount 240 and the back surface 232b of the support member 232. The bite block 236 is formed of a body 231 having a front surface which is integrally formed with the back surface 232b of the support member 232, an opposite back surface 242, a leading end surface 244 extending between the front and back surfaces, a trailing end surface 246 extending between the front surface and the mount 240, and opposite surfaces 248, 250 which form upper and lower surfaces depending upon which side of the mouth the sensor holder 220 is used. The distance between the opposite surfaces 248, 250 defines a height of the bite block 236. The bite block 236 preferably has a height which is less than the support member 232.

Each body 231 is shaped such that the leading end surface 244 provides a recess 252 which accommodates any structure 54 mounted on a patient's tooth, such as a clamp for a dental dam, therein as shown in FIG. 10. The shape of the body 231 is not critical, other than the leading end surface 244 provides the recess 252. That is, the leading end surface 244 has a first section 244a which is shaped to abut against a side of the structure 54 and has a second section 244b which extends around and overlaps an outer side of the structure 54. The rear surface 232b of the support member 232 is proximate to the inner side of the structure 54. As shown in a preferred embodiment, the bite block 236 generally looks like a "shark fin", with first and second sections 244a, 244b that extend along the same curve, and a back surface 242 which curves outwardly and toward the mount 240. As such, the shape of the bite block 236 generally mimics the dental arch of the patient.

When the sensor holder 220 is inserted into a patient's mouth, the patient is able to bite down with the patient's teeth on the surfaces 248, 250 of the bite block 236. The bite block 236 allows for more accurate positioning of the sensor holder 220, and more specifically the sensor 28, within a patient's mouth. The bite block 236 may include a series of serrations 262 in order to provide additional grip and less movement for the sensor holder 220 within the patient's mouth. The serrations 262 may be lines and are indented into the bite block 236. The serrations may take a variety of other forms, such as diamond-shaped, cubes, straight lines etc. As shown, the trailing end surface 246 curves outwardly and toward the mount 240. Curving this trailing end surface 246 may increase patient comfort as the patient's tongue may brush against this curved surface.

The retention assembly 234 includes first and second retention guides 270, 272 extending from the front side 232a of the support member 232. The first retention guide 270 extends from the front side 232a of the support member 232 proximate to the first end 232e of the support member 232. The second retention guide 272 extends from the front side 232a of the support member 232 at the second end 232f of the support member 232. Preferably, each retention guide 270, 272 is formed from a generally L-shaped cross-section having an extending portion 282 which extends perpendicularly relative to the support member 232 and a gripping portion 284 which extends perpendicularly from or curves inwardly toward the extending portion 282 and is parallel to or curves inwardly toward the support member 232. Each retention guide 270, 272 as described herein with regard to the first embodiment. The radiation sensing device 24 may be mounted between the retention guides 270, 272. Preferably, the gripping portions 284 apply enough pressure on the radiation sensing device 24 to hold the radiation sensing device 24 in place without damaging the radiation sensing device 24. When the radiation sensing guide 24 is mounted between the retention guides 270, 272, the sensor 28 preferably is positioned such that the majority of the sensor 28 is above or below the support member 232. The height of the bite block 236 is significantly smaller than the height of the gripping portions 284 so that a large amount of material of the bite block 236 is not present behind the sensor 28, thereby lessening the impact of the material of the bite block 236 on the image taken.

In operation, the radiation sensing device 24 is inserted into the retention guides 270, 272. The sensor holder 220 and the attached radiation sensing device 24 are then inserted into the mouth of the patient. During insertion of the sensor holder 220 into the patient's mouth, the sensor holder 220 is inserted with the leading end surface 244 of the bite block 236 first going into the mouth, with the trailing end surface 246 following. The bite block 236 passes over the teeth of the patient and the support member 232, the retention guides 270, 272 and the radiation sensing device 24 are in the interior of the mouth. There is nothing aligned with the bite block 236 along the length of the sensor holder 220 between the end 232e of the sensor holder 220 and the bite block 236. Therefore, the sensor holder 220 can be easily inserted into the mouth of the patient merely by sliding the sensor holder 220 into the mouth until bite block 236 is properly positioned or the bite block 236 encounters an obstacle, such as structure 54, in the mouth. When the bite block 236 is correctly positioned, the patient bites down onto the bite block 236 to securely hold the sensor holder 220 in place. If the patient has structure 54, such as a clamp, on a tooth to be x-rayed, when the bite block 236 encounters the structure 54, the structure 54 seats within the recess 252. The bite block 236 partially surrounds and engages the structure 54 ensuring a proper fit.

If desired, a removable insert 251 can be attached to the bite block 236 in the recess 252. The insert 251 is formed from a curved base wall 253 having a first curved shoulder 255 extending outwardly therefrom at a first end of the base wall 253, a second curved shoulder 257 extending outwardly therefrom at a second end of the base wall 253, and an intermediate curved shoulder 259 extending outwardly therefrom. The intermediate shoulder 259 is closer to the first shoulder 255 than to the second shoulder 237. A groove 261 is formed between the first shoulder 255 and the intermediate shoulder 259. The groove 261 has the approximately the same thickness as the height of the bite block 236.

The surfaces 244a, 244b of the bite block 236 seat within the groove 261 to attach the insert 251 to the bite block 236. The insert 251 is preferably held on the bite block 236 by a friction fit. The insert 251 can be attached to the bite block 236 in two positions. First, the insert 251 can be attached such that the intermediate shoulder 249 is proximate to the surface 248 of the bite block 236. In a second position, the insert 251 can be attached such that the intermediate shoulder 249 is proximate to the surface 250 of the bite block 236. In an endodontic procedure such as a root canal, an endo file(s) (not shown) may be in a tooth. The insert 251 surrounds the tooth being worked on so that the endo file(s) are not touched by the other teeth of the patient. In order to take an x-ray, the patient bites onto the end of the insert 251 having the second shoulder 257. This protects the endo file(s) while in the tooth.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

What is claimed is:

1. A sensor holder configured to retain a dental x-ray radiation sensing device comprising:

an elongated support member having first and second opposite ends, first and second opposite sides, and a longitudinal axis defined between the first and second ends;

a first retention guide extending from the first side of the support member and proximate to the first end;

a plunger movably attached to the first side of the support member, the plunger being movable to be positionable in a variety of positions along the longitudinal axis of the support member;

a second retention guide mounted on the plunger and spaced longitudinally from the first retention guide, the second retention guide movable with the plunger along the longitudinal axis; and a bite block extending from the second side of the support member, the bite block having surfaces configured to be engaged by a user's upper and lower teeth, the surfaces extending in a longitudinal direction which is parallel to the longitudinal axis.

2. The sensor holder of claim 1, further comprising third and fourth retention guides attached to the support member.

3. The sensor holder of claim 1, wherein the bite block includes an upper surface and a lower surface against which a wearer's teeth are configured to engage, an outer frame having an aperture therethrough, the aperture extending from the upper surface to the lower surface, and an insert formed of an elastomeric material, the insert being seated within the aperture in the outer frame and filling the aperture, the insert being removable from the outer frame.

4. A sensor holder configured to retain a dental x-ray radiation sensing device comprising:
   an elongated support member;
   a first retention guide extending from the support member;
   a first plunger movably attached to the support member;
   a second retention guide mounted on the first plunger;
   a third retention guide extending from the support member;
   a second plunger movably attached to the support member;
   a fourth retention guide mounted on the second plunger; and
   a biasing member between the first and second plungers.

5. The sensor holder of claim 4, wherein the first and second retention guides are spaced apart from each other by a first distance, and the third and fourth retention guides are spaced apart from each other by a second distance, wherein the first distance is less than the second distance.

6. The sensor holder of claim 4, wherein the biasing member is one of an elastomeric member and a spring.

7. The sensor holder of claim 4, further comprising at least one bite block attached to the support member.

8. The sensor holder of claim 7, wherein the at least one bite block attached to said support member has a leading edge which is first inserted into a mouth of a patient and a trailing edge, the leading edge defining a recess into which structure within the mouth of the patient can seat, the recess is formed by a first surface which extends a front side of a tooth of the user and a second surface which extends around an outer side of the tooth of the user.

9. The sensor holder of claim 8, wherein the first and second surfaces are curved.

10. The sensor holder of claim 9, wherein the trailing edge is curved.

11. The sensor holder of claim 8, wherein the first surface is angled relative to the support member and the second surface is angled relative to the first surface.

12. The sensor holder of claim 11, wherein the trailing edge is curved.

13. The sensor holder of claim 8, wherein the bite block has a height which is substantially the same as or less than the support member.

14. The sensor holder of claim 8, wherein the support member is attached to a mount configured to mount a ring guide to the sensor holder.

15. The sensor holder of claim 8, wherein the bite block includes an outer frame and an insert which seats within the outer frame and is removable from the outer frame, the insert being formed from an elastomeric material.

16. The sensor holder of claim 8, further comprising an insert attached to the leading edge, the insert being removable from the leading edge.

* * * * *